US011801774B2

(12) United States Patent
Lu-Dac et al.

(10) Patent No.: US 11,801,774 B2
(45) Date of Patent: *Oct. 31, 2023

(54) METHOD AND SYSTEM FOR UNATTENDED CHILD DETECTION

(71) Applicant: IEE INTERNATIONAL ELECTRONICS & ENGINEERING S.A., Echternach (LU)

(72) Inventors: Mathieu Lu-Dac, Luxembourg (LU); Patrick Di Mario Cola, Serrouville (FR); Dimitri Tatarinov, Trier (DE); Andreas Diewald, Kell am See (DE); Claude Watgen, Sandweiler (LU); Sam Calmes, Luxembourg (LU); Peter Larsen, Bereldange (LU)

(73) Assignee: IEE INTERNATIONAL ELECTRONICS & ENGINEERING S.A., Echternach (LU)

( * ) Notice: Subject to any disclaimer, the term of this patent is extended or adjusted under 35 U.S.C. 154(b) by 403 days.

This patent is subject to a terminal disclaimer.

(21) Appl. No.: 16/663,691

(22) Filed: Oct. 25, 2019

(65) Prior Publication Data

US 2020/0180472 A1 Jun. 11, 2020

Related U.S. Application Data

(63) Continuation of application No. 15/127,700, filed as application No. PCT/EP2015/056017 on Mar. 20, 2015, now Pat. No. 10,457,161.

(30) Foreign Application Priority Data

Mar. 21, 2014 (LU) .................................. LU 92 410

(51) Int. Cl.
*B60N 2/00* (2006.01)
*A61B 5/0507* (2021.01)
(Continued)

(52) U.S. Cl.
CPC ............ *B60N 2/002* (2013.01); *A61B 5/0507* (2013.01); *A61B 5/113* (2013.01); *A61B 5/4809* (2013.01);
(Continued)

(58) Field of Classification Search
CPC ........ G01S 13/04; G01S 13/50; G01S 13/505; G01S 13/56; G01S 13/92; G01S 13/62;
(Continued)

(56) References Cited

U.S. PATENT DOCUMENTS

| 5,482,314 A | 1/1996 | Corrado et al. |
| 6,753,780 B2 * | 6/2004 | Li ........................ B60N 2/002 180/271 |

(Continued)

FOREIGN PATENT DOCUMENTS

| WO | WO-2009083017 A1 * | 7/2009 | ............. G01S 13/50 |
| WO | WO2009083017 A1 | 7/2009 | |

OTHER PUBLICATIONS

International Search Report for International application No. PCT/EP2015/056017, dated Jun. 10, 2015, 2 pages.
(Continued)

*Primary Examiner* — Mvladimir Magloire
*Assistant Examiner* — Michael W Justice
(74) *Attorney, Agent, or Firm* — REISING ETHINGTON P.C.

(57) ABSTRACT

A radar sensor system and method for ascertaining whether an unattended child is present within an automotive vehicle. The radar sensor system carries out the method and includes a transmitter, at least one sensor, and processing circuitry. The method includes the steps of: illuminating at least one occupiable position within the vehicle with radiation of multiple frequencies; generating radar sensor signals from reflections of the transmitted radiation, a plurality of the (Continued)

radar sensor signals corresponding to different frequencies; and operating the processing circuitry for generating and determining if a first indicator value indicative of motion in the occupiable position satisfies a first predetermined criteria and, if so, generating and determining a second indicator value indicating a degree of repetitive pattern within the radar sensor signals, and determining presence of an unattended child in the vehicle if the second indicator value satisfies a second predetermined criteria.

20 Claims, 12 Drawing Sheets

(51) Int. Cl.
| | |
|---|---|
| *A61B 5/00* | (2006.01) |
| *A61B 5/113* | (2006.01) |
| *B60N 2/26* | (2006.01) |
| *B60N 2/28* | (2006.01) |
| *G01S 13/56* | (2006.01) |
| *G01S 13/04* | (2006.01) |
| *G01S 7/41* | (2006.01) |

(52) U.S. Cl.
CPC .............. *A61B 5/6893* (2013.01); *B60N 2/26* (2013.01); *B60N 2/286* (2013.01); *G01S 13/04* (2013.01); *G01S 13/56* (2013.01); *A61B 2503/06* (2013.01); *G01S 7/412* (2013.01)

(58) Field of Classification Search
CPC .......... G01S 13/931; G01V 3/00; G01V 3/06; G01V 3/12; G01V 3/15; B60N 2/002; B60N 2/26; B60N 2/2866; A61B 5/0507; A61B 5/113; A61B 5/4809; A61B 5/6893; A61B 2503/06
USPC .......................................................... 342/28
See application file for complete search history.

(56) References Cited

U.S. PATENT DOCUMENTS

| | | | |
|---|---|---|---|
| 7,036,390 B2 | 5/2006 | Tsuchihashi et al. | |
| 7,520,529 B2* | 4/2009 | Hofbeck | ........... B60R 21/01534 |
| | | | 280/735 |
| 8,725,311 B1* | 5/2014 | Breed | .................. A61B 5/0507 |
| | | | 701/1 |
| 10,457,161 B2 | 10/2019 | Lu-Dac et al. | |
| 2001/0042976 A1* | 11/2001 | Breed | ................. G01F 23/2962 |
| | | | 280/735 |
| 2002/0140214 A1 | 10/2002 | Breed et al. | |
| 2003/0038712 A1 | 2/2003 | Pelletier | |
| 2003/0201894 A1* | 10/2003 | Li | .......................... B60N 2/002 |
| | | | 340/573.1 |
| 2003/0209893 A1* | 11/2003 | Breed | .................. B60N 2/0248 |
| | | | 280/735 |
| 2009/0046538 A1 | 2/2009 | Breed et al. | |
| 2010/0069745 A1 | 3/2010 | Muehlsteff et al. | |
| 2012/0089299 A1 | 4/2012 | Breed | |
| 2013/0113647 A1 | 5/2013 | Sentelle et al. | |

OTHER PUBLICATIONS

Written Opinion for International application No. PCT/EP2015/056017, dated Jun. 10, 2015, 7 pages.
English Translation of Chinese Office Action corresponding to application No. 201580022515.4, dated Jan. 22, 2019, 15 pages.

\* cited by examiner

| Age | Average resting breathing rate (bpm) |
|---|---|
| Birth to 6 weeks | 30-60 |
| 6 months | 25-40 |
| 3 years | 20-30 |
| 6 years | 18-25 |
| adults | 12-20 |
Fig. 12
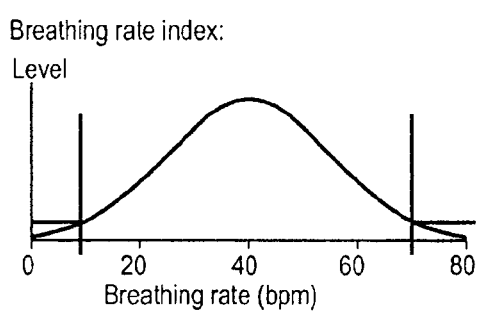
Fig. 13A
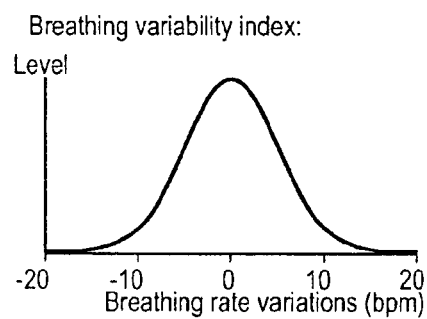
Fig. 13B
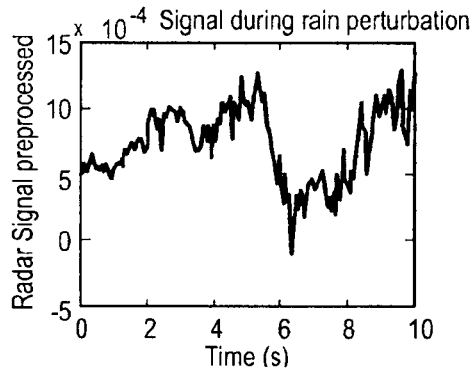
Fig. 15A
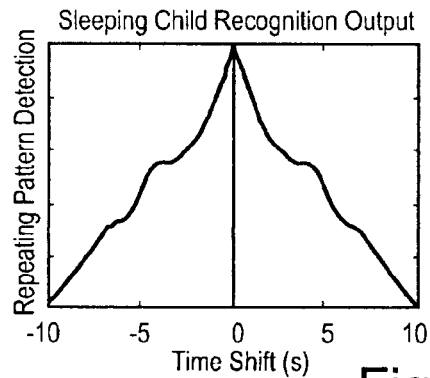
Fig. 15B
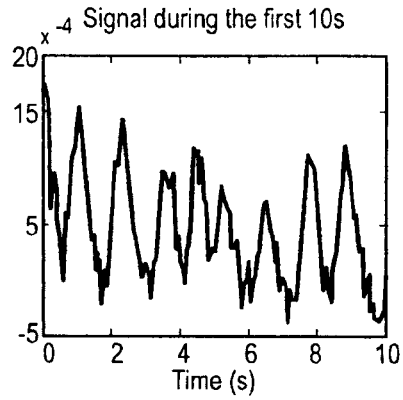
Fig. 16A
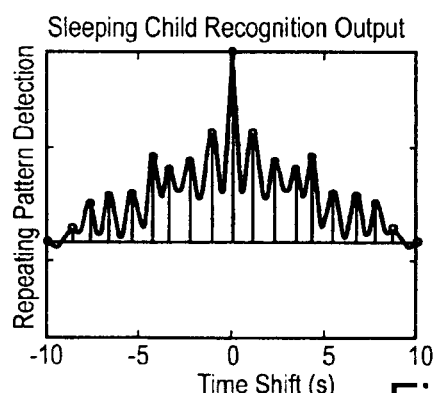
Fig. 16B

METHOD AND SYSTEM FOR UNATTENDED CHILD DETECTION

TECHNICAL FIELD

The present invention relates to radar-based detection of humans within an automotive vehicle, and more particularly to a method and system for detection of sleeping/unattended children in such environments.

BACKGROUND ART

Systems for occupant detection and classification in cars are known.

In addition, radar-based seat belt reminder sensors and the use of the "R-Value" concept are known. Detectors that act as monitors for (sleeping) babies in their rooms are also available.

Techniques for detection of humans in vehicles based on breathing detection have been described previously. For example, U.S. Pat. No. 6,753,780 discloses motion sensing system and method for detecting an occupant in a vehicle with sensitivity to detect small movement, such as movement caused by heartbeat and breathing. A radar motion sensor located in a compartment of the vehicle transmits and receives signals and generates sensed signals. A controller converts the sensed signals to a frequency domain. The controller further processes the frequency domain of sensed signals and determines the presence of movement of an occupant due to one of heartbeat and breathing of the occupant.

U.S. Pat. No. 7,036,390 discloses an in-vehicle body detection method in which a synthetic wave is obtained which represents the synthesis of a transmitted wave radiated from a sensor and a reflected wave returned from a breathing human body, and the presence or absence of a human in the vehicle is detected from the envelope of the synthetic wave. When the presence of a human is detected continuously for a predetermined length of time, it is determined that a human is present in the vehicle.

SUMMARY OF THE INVENTION

According to one aspect of the invention there is provided a method for ascertaining whether an unattended child is present within an automotive vehicle using a radar sensor system, the radar sensor system comprising a transmitter, at least one sensor and processing circuitry, the method comprising: illuminating, using the transmitter, at least one occupiable position within the vehicle with radiation, the radiation exhibiting at least one frequency; generating, using at least one sensor, radar sensor signals from radiation reflected as a result of the transmitted radiation, and possibly a plurality of the radar sensor signals corresponding to different frequencies; operating the processing circuitry for generating, based on the radar sensor signals, a first indicator value, the first indicator value indicating a degree of motion associated with the occupiable position, determining whether the first indicator value satisfies a first predetermined criteria, if the first indicator value satisfies the first predetermined criteria, generating, based on radar sensor signals, a second indicator value, the second indicator value indicating a degree of repetitive pattern within the radar sensor signals, and determining that an unattended child is present within the automotive vehicle if the second indicator value satisfies a second predetermined criteria.

Several modes are possible for the radar frequency. In a pseudo Continuous Wave mode, the radar sensor system is illumination the scene with a constant output frequency (called Continuous Wave CW mode) possibly with temperature drift, temperature compensation, fingerprint, random selection or self-diagnostic. In a slow sweep mode, the radar sensor system is illuminating the scene with an output frequency which is changing slowly over time (called FMCW in slow mode). In a multiple frequency mode, the radar sensor system is illuminating the scene with output frequencies which are modulated by a defined function such as e.g. saw tooth (typical FMCW). Alternatively in a three frequency mode, the radar sensor system is illuminating the scene with 3 predefined frequencies according to a pattern based order.

The first predetermined criteria may be that the first indicator value lies between a first threshold value (R1) and a second threshold value (R2).

The first indicator value may comprise an R-value, corresponding to an amplitude of variation of the pre-processed reflected radar sensor signals.

The second predetermined criteria may be that the second indicator value lies above a third threshold value.

The second indicator value may be dependent upon a breathing rate index, the breathing rate index being derived from motion determined based on the radar sensor signals.

The second indicator value may be dependent upon a breathing rate variation index, the breathing rate variation index being derived from motion determined based on the radar sensor signals and indicating a degree of variation in breathing rate.

The second indicator value may be or is derived from the product of multiple breathing indices, each breathing index being related to breathing rate.

In a possible embodiment, the second indicator value may be a function combining both the breathing rate and breathing rate variation index. The second indicator value may for instance be generated as the product: k×breathing rate index×breathing rate variation index, where the breathing rate index is derived from motion determined based on the radar sensor signals, the breathing rate variation index is derived from motion determined based on the radar sensor signals and indicating a degree of variation in breathing rate, and k is a constant. In one embodiment, k is 100 and the lower threshold value is approximately 20.

The second indicator value may comprise a breathing signature indicative of the extent to which the sensor signals indicate that motion indicative of infant breathing child is detected.

In one embodiment, determining whether the first indicator value satisfies a first predetermined criteria is performed based on radar sensor signals occurring during a first predetermined period following initiation.

In one embodiment, determining that an unattended child is present within the automotive vehicle if the second indicator value satisfies a second predetermined criteria is based on radar sensor signals occurring during a second predetermined period following initiation. Preferably, the second predetermined period is longer than the first predetermined period. Preferably, the first predetermined period is has a duration lying in the range 5-10 seconds and the second predetermined period has a duration lying in the range 10-30 seconds.

In the multiple frequency mode, the radar sensor signals may be derived from a combination of multiple received signals resulting from the radiation, the received signals being at different frequencies. In other variants, the frequencies are not varied as a function of the results of the decision algorithm but could be a function of temperature, signal to noise ratio or detection of destructive interferences.

The frequencies of the transmitted radiation may be dynamically varied whereby (i) determining whether the first indicator value satisfies a first predetermined criteria is and/or (ii) determining that an unattended child is present within the automotive vehicle if the second indicator value satisfies a second predetermined criteria is time optimized.

Preferably (i) the first threshold value is such that the first indicator value being below the first threshold value is indicative of an empty seat or environment, (ii) the second threshold value is such that the first indicator value being above the second threshold value is indicative of a moving person or child, and/or (iii) the first threshold value the second threshold value are such that the first indicator value being between the first threshold value the second threshold value is indicative of a sleeping child being present in the occupiable position or of strong influence from sources external to the vehicle.

According to another aspect of the invention there is provided a programmable radar sensor system when suitably programmed for carrying out the method of any of the preceding claims for sensing occupancy status within an automotive vehicle, the radar sensor system comprising a transmitter, at least one sensor and processing circuitry for performing the method.

According to another aspect of the invention there is provided a radar sensor system for ascertaining whether an unattended child is present within an automotive vehicle, the system comprising: a transmitter, for illuminating at least one occupiable position within the vehicle with radiation, the radiation exhibiting multiple frequencies; least one sensor (10) for generating radar sensor signals from radiation reflected as a result of the transmitted radiation, a plurality of the radar sensor signals corresponding to different frequencies; processing circuitry (18), coupled to the at least one sensor (10), the processing circuitry being operable for generating, based on the radar sensor signals, a first indicator value, the first indicator value indicating a degree of motion associated with the occupiable position; determining whether the first indicator value satisfies a first predetermined criteria; if the first indicator value satisfies the first predetermined criteria, generating, based on radar sensor signals, a second indicator value, the second indicator value indicating a degree of repetitive pattern within the radar sensor signals; and determining that an unattended child is present within the automotive vehicle if the second indicator value satisfies a second predetermined criteria.

According to another aspect of the invention there is provided a recordable, rewritable or storable medium having recorded or stored thereon data defining or transformable into instructions for execution by processing circuitry and corresponding to at least the steps of any of claims 1 to 16 of the appended claims.

According to another aspect of the invention there is provided a server computer incorporating a communications device and a memory device and being adapted for transmission on demand or otherwise of data defining or transformable into instructions for execution by processing circuitry and corresponding to at least the steps of any of claims 1 to 16 of the appended claims.

In embodiments, the present invention operates to analyze the received signals of a pseudo Continuous Wave Radar (slowly drifting due to temperature) or a fingerprinted Continuous Wave Radar (frequency set in hardware), or self-calibrated Continuous Wave Radar (by signal to noise ratio or temperature compensation) or a Frequency Modulated Continuous Wave Radar or a Frequency Shift keying Radar, from humans (typically children) and classify them into 4 different groups: Moving children, Sleeping newborns (babies/infants), Outside influences and empty environment. This classification may involves two different types of processing—

Derivation of R-value as a general representation of human motion, and sleeping child recognition (detection) as a more complex characterization of the human radar signature.

In embodiments, the present invention operates to perform detection of humans by recognition of their vital sign signatures, detection of movements of children, detection of unattended child detection in cars, detection and measurement of breathing with radar based technology and signal processing. Thus, in embodiments the present invention provides discrimination between humans (sleeping children) and outside influences (external perturbations).

BRIEF DESCRIPTION OF THE DRAWINGS

Preferred embodiments of the invention will now be described, by way of example, with reference to the accompanying drawings, in which:

FIG. 3 includes FIG. 3A and FIG. 3B, in which

FIG. 12 shows resting breathing rates for humans of various ages;

FIG. 13 includes FIG. 13A and FIG. 13B, in which FIG. 13A shows the distribution of a breathing rate index and FIG. 13B shows the distribution of a breathing variability index;

FIG. 15 includes FIG. 15A and FIG. 15B, each of which shows signals produced using the algorithm of FIG. 14, in a case where a baby is present; and FIG. 16 includes FIG. 16A and FIG. 16B, each of which shows signals produced using the algorithm of FIG. 14, in a case of a rain test with an empty car.

DESCRIPTION OF PREFERRED EMBODIMENTS

In order to address the aforementioned problems, the present invention proposes to use a radar-based system able to detect children in a car. The action to be taken in response to such detection may be a (e.g. audible) reminder for the driver not to leave his child alone, the automatic regulation of the car temperature, or even an emergency call initiation.

Figure 1:
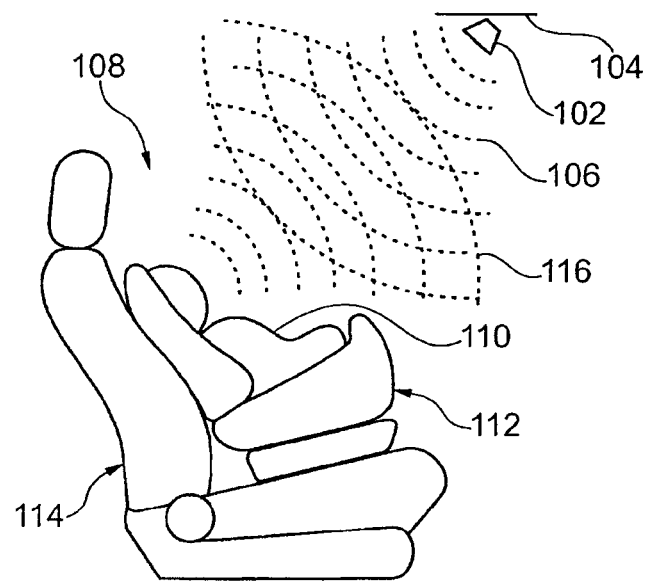
FIG. 1 shows the physical disposition within the cabin of a vehicle of elements of the detection system according to the embodiments of the invention.

FIG. 1 shows the physical disposition within the cabin of a vehicle of elements of the detection system according to the embodiments of the invention. A transceiver 102 mounted on the ceiling 104 of the vehicle directs RF radiation 106 at an occupyable position 108 within the vehicle. In this case, occupyable position 108 is occupied by a baby 110 on a baby seat 112 mounted on car seat 114. Reflected radiation 116 reflected of the baby 110 is received by transceiver 102.

Figure 2:
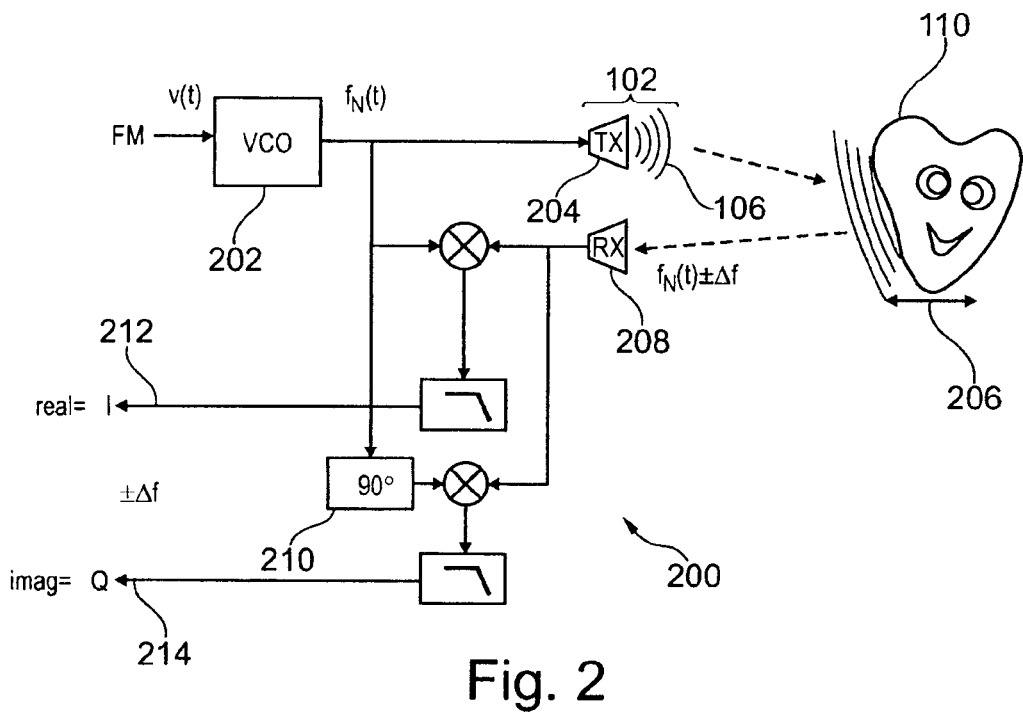
FIG. 2 schematically illustrates radar signal transition and reception techniques employed in embodiments of the present invention, using a radar sensor system 200.

FIG. 2 schematically illustrates radar signal transition and reception techniques employed in embodiments of the present invention, using a radar sensor system 200. A frequency modulation signal controls VCO 202 which provides multiple or varying frequencies $f_N(t)$ to transmitter 204 forming part of transceiver 102. As a result of the motion (e.g. breathing) generally designated 206 of baby 110, the received radiation 116 received at receiver 208 of transceiver 102 has a frequency given by $f_N(t) \pm \Delta f$. As is well known in relation to radar systems, the Doppler frequency may be given by $$\Delta f = \frac{\Delta v}{c} f_0$$

As also well known, demodulators and filters together with a shift element 210 providing a 90° shift provides received signals in the form of real (I) and imaginary (Q) signals on separate channels 212 and 214, respectively. The transmitted radiation is preferably FMCW/FSK radar signals where the frequency can be tuned.

Embodiments are based on a Frequency Modulated Continuous Wave (FMCW) or Frequency Shift Keying (FSK) Radar module that emits in a particular bandwidth (24-24.25 GHz currently but other frequency ranges may be used).

Figures 3A, 3B:
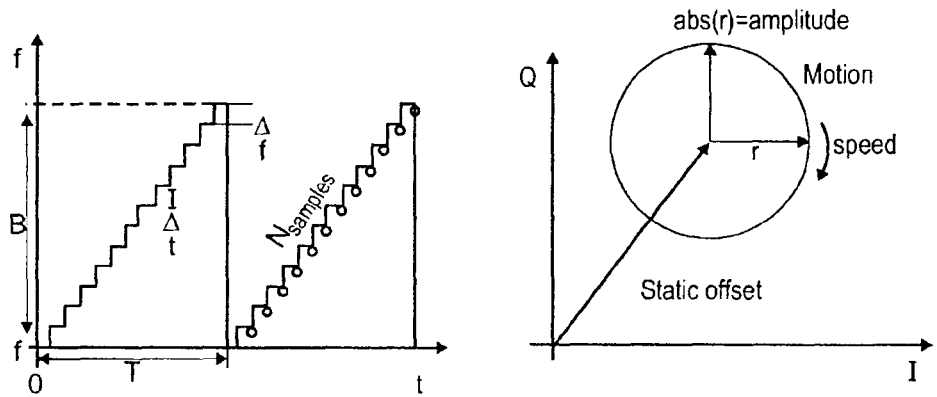
FIG. 3A shows a waveform for the transmitted frequencies, and corresponding samples.
FIG. 3B shows a plot of I and Q channel signals providing a circle in the complex domain, for the radar sensor system 200 of FIG. 2.

A waveform for the transmitted frequencies, and corresponding samples, is illustrated in FIG. 3A. A plot of I and Q channel signals provide a circle in the complex domain. This is illustrated in FIG. 3B, whereby a static offset caused by the static environment. The static offset can be removed by filtering or by circle estimation. The amplitude of the received signal is derived from the radius (abs(r)) of the circle, and this is equivalent to the R-value. The speed of rotation of R corresponds to the Doppler frequency, thus describing the speed and direction of movement of the target (e.g. baby). In relation to the received signals, this may be expressed as $$u(t) = A \exp\left(j \frac{2\omega_t}{c}(\dot{r}t + r_0) - j\theta_r\right)$$

where the term $\dot{r}t$ is used to provide the Doppler information. The R-value is the translation in polar coordinates of the IQ cathesian modulation where the origin of the coordinates is set to the center of the circle (or where the offset due to hardware and scene is filtered out).

Thus, based on the radar signals, a first measure of motion is extracted: the "R-Value". This value takes into account most kinds of motion but is centered on "human motion", to limit the higher frequency noises as well as the much lower frequencies influences that might come from slower processes (e.g. drift inherent of the system or other slow external processes). The R-value is important as it can be used to determine whether a sleeping/unattended baby or child is present.

Figure 4:
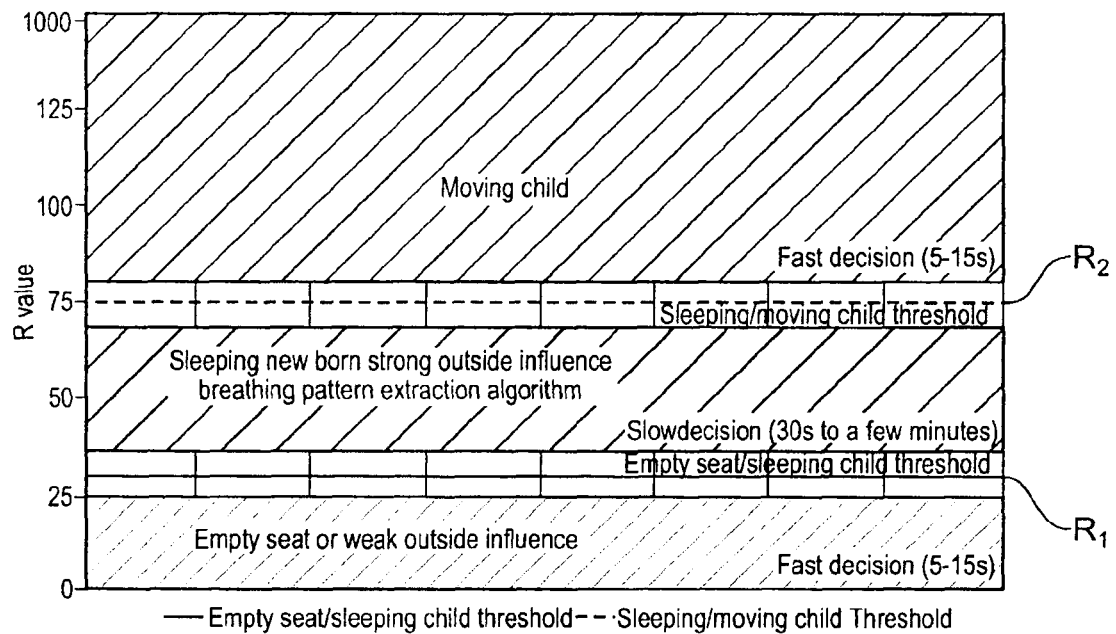
FIG. 4 shows how ranges of R-Value can be used to distinguish between humans and outside influences in most cases.

FIG. 4 shows how ranges of R-Value can be used to distinguish between humans and outside influences in most cases.

An R-value below a first (lower) threshold $R_1$ is indicative of an empty seat (also known as an empty environment) or weak external influence. A very weak R-Value (typically below the Empty Seat/Sleeping Child threshold) is characteristic of an environment devoid of any human presence: empty seat or weak outside influences (lowermost zone in FIG. 4). This classification is called "Empty Environment Recognition".

An R-value above an upper threshold $R_2$ is indicative of a moving child being present. A very high R-value Value (typically above the Sleeping Child/Moving threshold) is characteristic of human motions like limb movement or larger child/adult breathing (uppermost zone in FIG. 4). This classification is called "Moving Child Recognition".

Finally, an R-value lying between $R_1$ and $R_2$ is inconclusive: there is either a sleeping baby present or a strong influence from external sources; and a subsequent breathing pattern extraction algorithm must be executed in accordance with embodiments of the invention to determine which is the case.

Between the two thresholds, the R-values can be either caused by a sleeping child (typically a newborn) but could be as well be caused by outside influences (car passing by, rain, pedestrian close to the car, sunshield on the external part of the window moving with the wind etc.). In this (intermediate) region, a more sophisticated type of processing is needed, in order to distinguish the human signals from outside influences—Sleeping Child Recognition (SCR).

Figure 5:
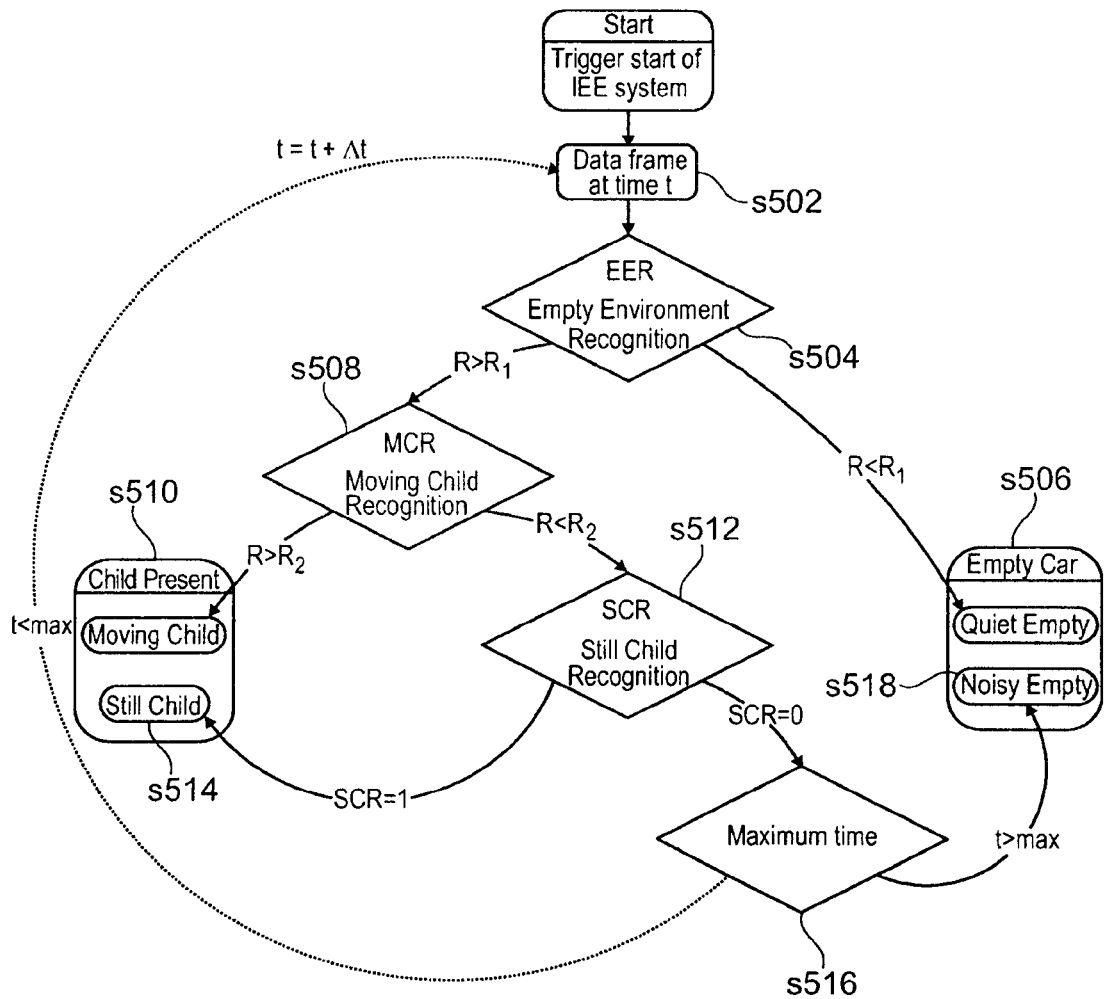
FIG. 5 is a general overview of algorithm processing in accordance with embodiments of the invention.

FIG. 5 is a general overview of algorithm processing in accordance with embodiments of the invention. FIG. 5 shows the different steps involved in the classification from a comprehensive algorithm point of view. Starting with a data frame at time t (s502), a determination is made at s504, and if the R-value is less than $R_1$, a decision is made that there is an empty car (baby or other occupant not present), as indicated at s506. Otherwise, if it is determined at s504 that R is greater than $R_1$, there follows a moving child recognition step at s508. Here, if it is determined that the R-value is greater than $R_2$, a decision is made that a child is present (s510), i.e. a moving child.

If, on the other hand, it is determined at s508 that the R-value is less than $R_2$, processing proceeds with a sleeping child recognition (detection) step s512, discussed in further detail herein below. At s512, a determination that a sleeping child recognition value or index is equal to 1 max, a decision is taken that a still (unattended/sleeping) child is present within the vehicle (s514). If, at s512, the determined sleeping child recognition index is 0, a further determination is made at s516 such that, if t>max, a decision is made that the car is empty but noisy (s518). Where, however, t<max, processing returns to s502. This inconclusive loop is made to avoid babies to be "hidden" by external perturbations.

Figure 6:
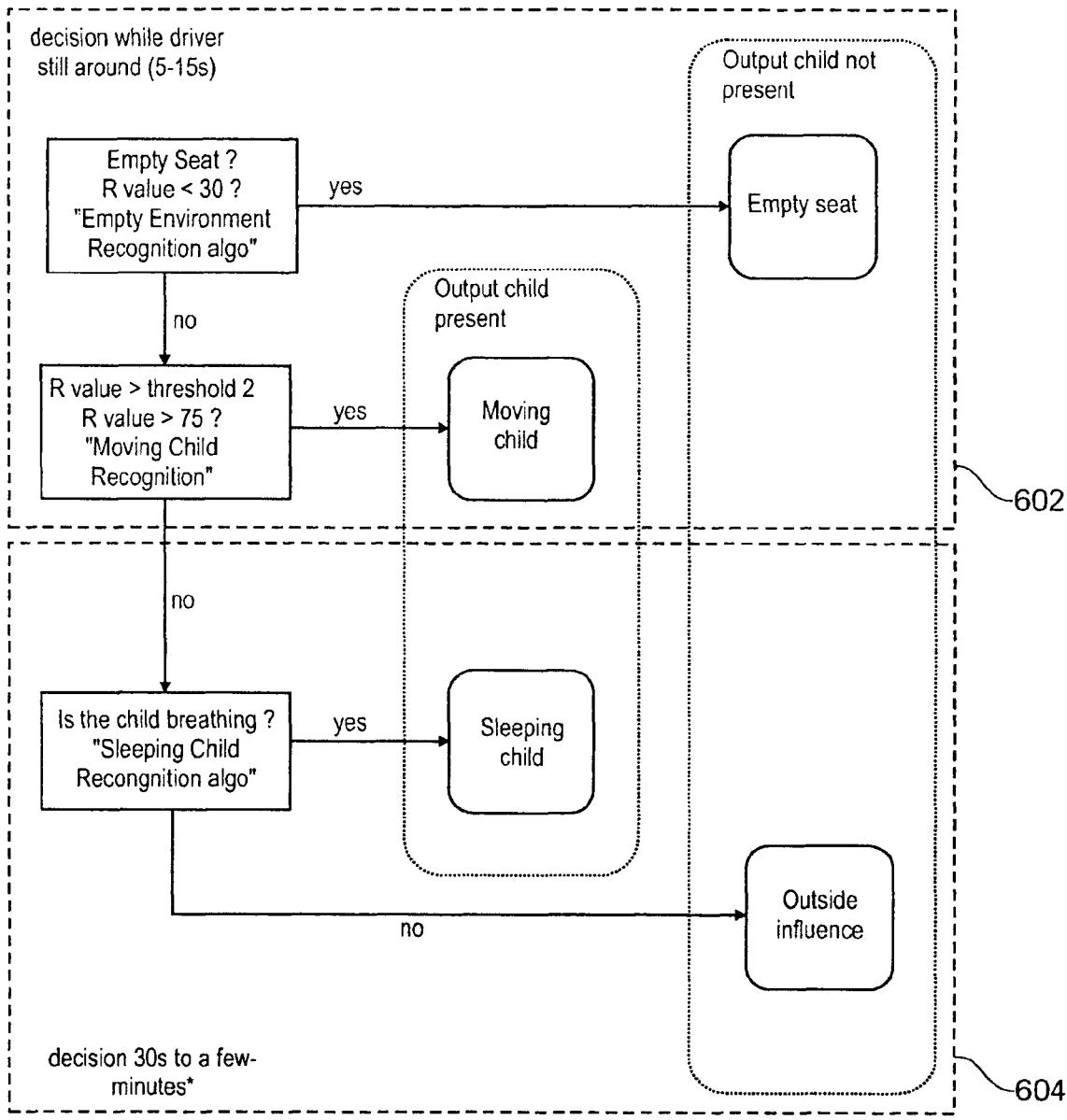
FIG. 6 illustrates states in the decision making process of FIG. 5.

Referring to FIG. 6, this illustrates states in the decision making process of FIG. 5, including values for thresholds ($R_1$ and $R_2$), as well as time periods for decisions to be made, in embodiments of the invention. In particular, decisions in the upper block 602 may be made rapidly, e.g. within 5 to 15 seconds (for example while the driver of the car is still around). On the other hand, the decisions in the lower block 604 (including whether a sleeping child is present) may be determined in a longer period, for example 30 seconds to a few minutes from initialization of the recognition algorithm.

FIG. 6 shows the two-step strategy regarding the timings: the fast decision involves only the EER and the MCR whereas the SCR requires a longer data acquisition and processing time. During execution of the Sleeping Child Recognition algorithm the Empty Environment Recognition and Moving child Recognition are also periodically evaluated in parallel. If an empty seat or a moving child is detected, the sensor output will jump immediately to "child not present"/"child present".

Figure 7:
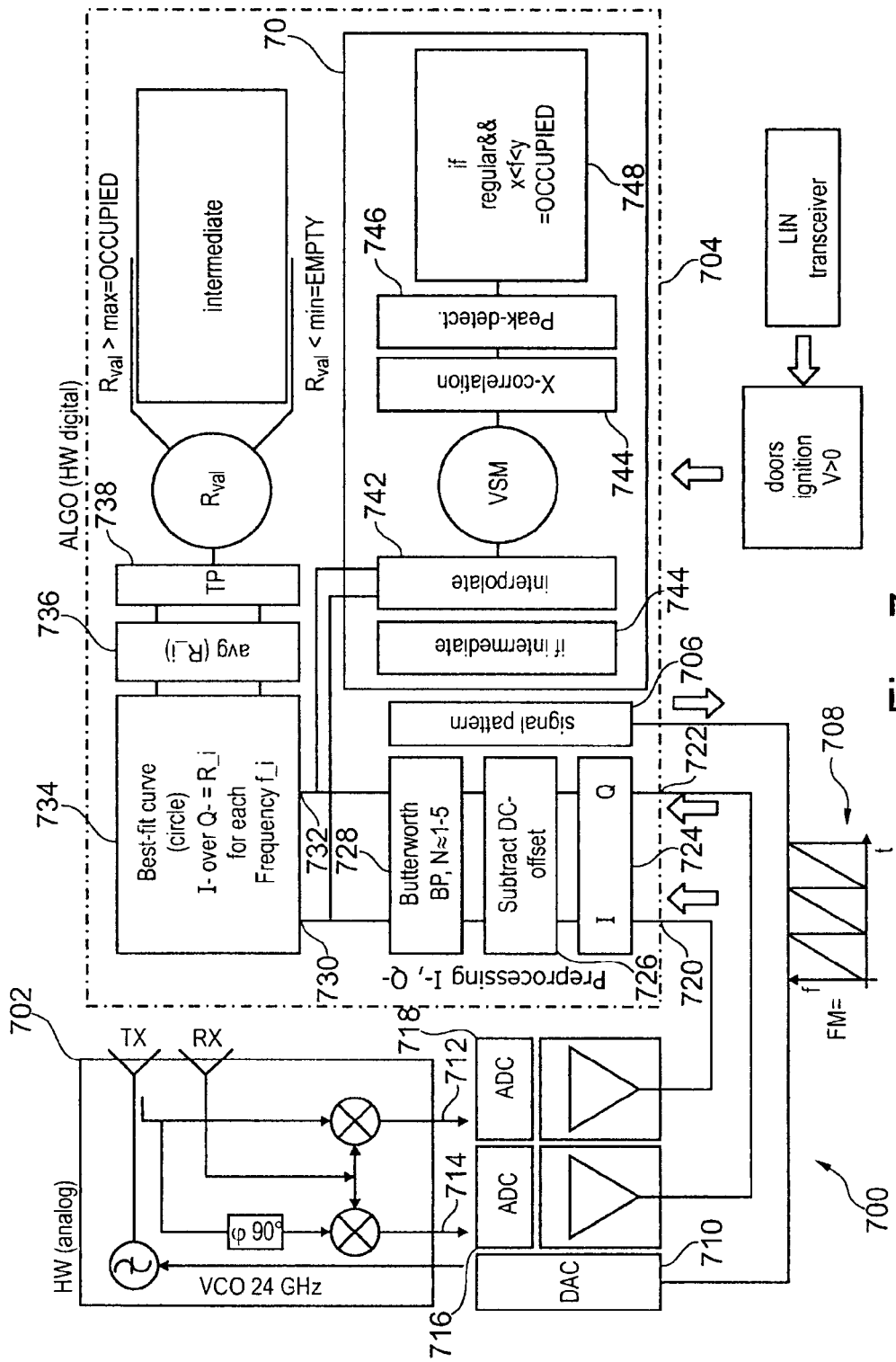
FIG. 7 is a schematic diagram of a sleeping child recognition system according to an embodiment of the invention.

FIG. 7 is a schematic diagram of a sleeping child recognition system according to an embodiment of the invention. This may include analog hardware block 702, corresponding generally to the circuitry of FIG. 2. Further, the system 700 may include signal processing circuitry 704: while the latter has been illustrated as hardware, it would be appreciated by person skilled in the art that signal processing circuitry 704 may be implemented as hardware, software or a combination of hardware and software.

Signal pattern unit 706 provides a command signal generally designated 708 that is fed via digital-to-analog unit (DAC) 710, which in turn provides a control signal to the VCO of analog transceiver block 702. Received radar sensor signals provided at outputs 712 and 714 of analog transceiver block 702 provide, via ADCs 716 and 718 I and Q signals, respectively, to inputs 720 and 722 of signal processing unit 704.

Within signal processing unit 704, buffer 724, DC-offset subtraction unit 726 and digital filter 728 (e.g. Butterworth with N approx. 1-5) provide preprocessing of the I and Q signals.

Principles of the SCR Algorithm:

To discriminate the sleeping child from outside influences, a new algorithm has been developed that takes into account the specificity of sleeping children, which requires processing the radar signal for a longer time.

At least in embodiments, the invention is based on the unexpected finding that the radar signature of a sleeping child incorporates a repetitive pattern due to the regularity of the breathing of the newborn. Indeed, despite the low R-value, the signal of the sleeping newborn child is recognizable by the regularity of its dominant frequencies, which are distinct from the system noise and outside influences.

Figure 8A:
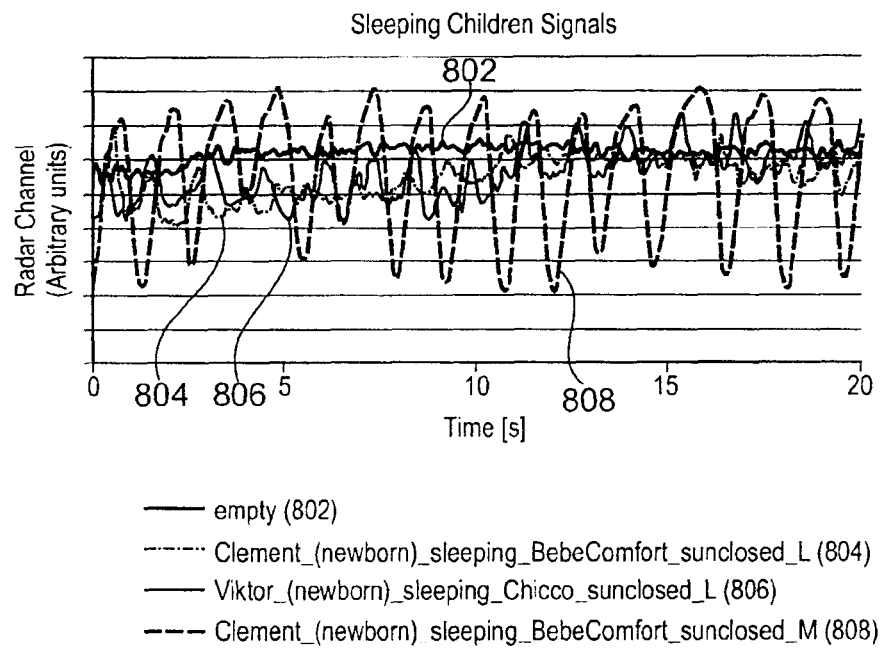
FIG. 8 includes FIG. 8A and FIG. 8B, which show, respectively, outputs of the preprocessing, for sleeping children and outside influences, in various scenarios.
Figure 8B:
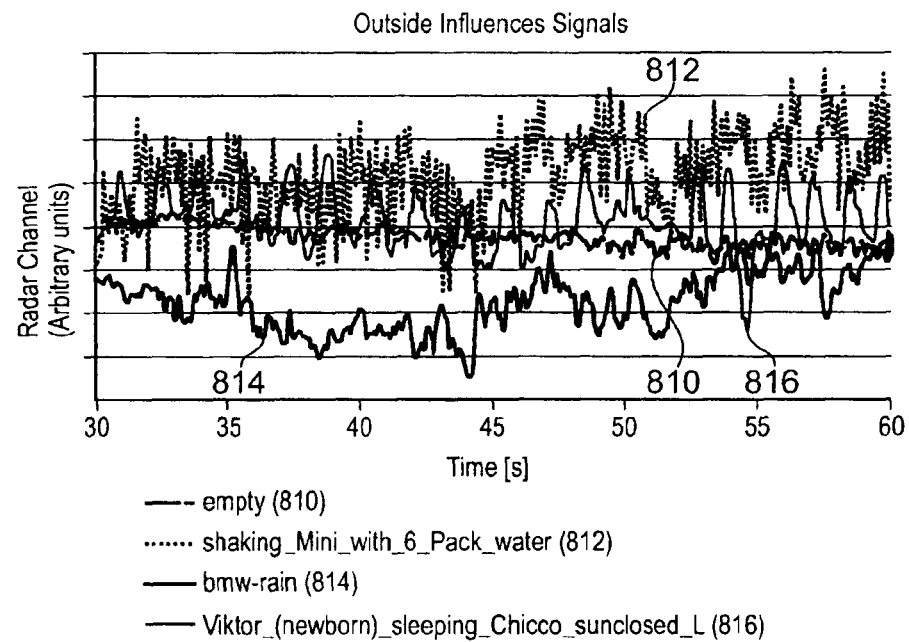

Referring to FIGS. 8A and 8B, these show, respectively, outputs of the preprocessing, for various scenarios involving the presence of sleeping children (FIG. 8A) and various scenarios involving external influences such as vehicle shaking with the presence of a pack of water, and the impact of rain.

As seen in FIGS. 8A and 8B, the breathing of the sleeping infant is clearly distinguishable either from influences coming from outside or signal signature on an empty seat. In FIG. 8A, the radar signals of sleeping children show the regular breathing patterns even for the worst cases. In FIG. 8B, the radar signals of outside influences compared to the sleeping newborn are very different.

Returning to FIG. 7, the preprocessed output signals (I, Q) are provided to inputs 730, 732, respectively, of curve fitting module 234 which performs a best fit (circle) matching operation. This is followed by an averaging operation on the $R_1$ values by averaging module 736 followed by final processing at TP module 738. The output of TP module 738 is the R-value, as discussed in relation to FIGS. 3 and 4 above. Again, an R-value above a maximum ($R_1$) indicates an occupied condition, whereas an R-value less than a minimum ($R_2$) indicates an empty condition as discussed in relation to FIGS. 5 and 6 above.

Figure 9A:
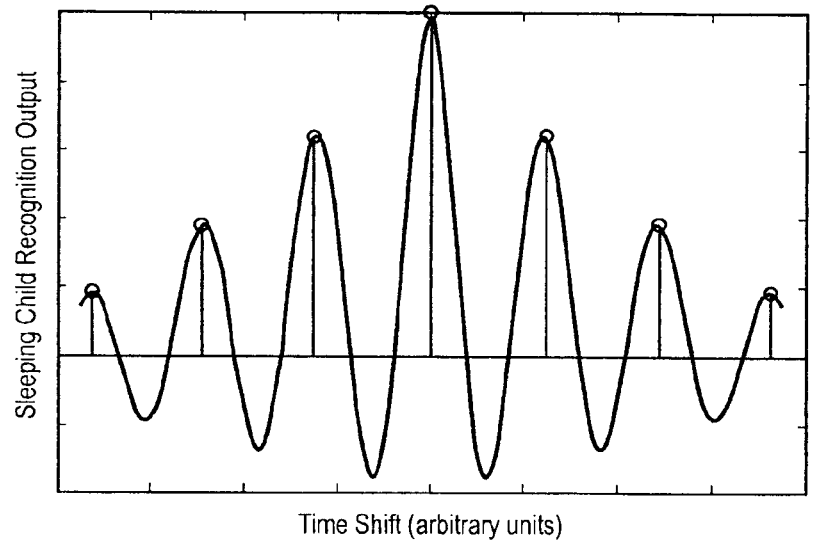
FIG. 9 includes FIG. 9A and FIG. 9B, which show examples of signatures in the case of a sleeping child being present.
Figure 9B:
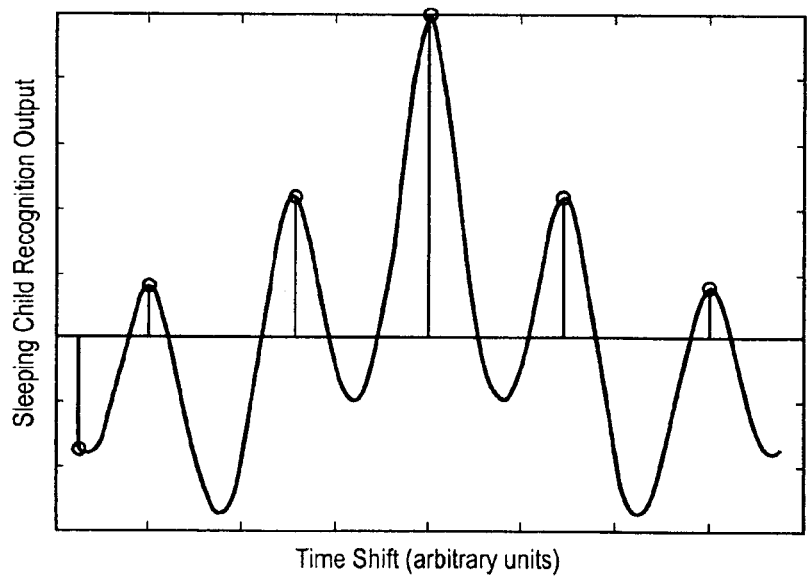

In the event that the R-value is intermediate those thresholds ($R_1$, $R_2$), further processing is carried out. More particularly, sleeping child recognition unit 740 receives the I, Q signals and then performs interpolation thereof using interpolation unit 742, if it is determined by comparison unit 744 that the R-value is intermediate. The output of interpolation unit 742 is a signature waveform (or "signature"), also referred to herein as VSM. Examples of signatures in the case of a sleeping child being present are shown in FIGS. 9A and 9B. FIG. 9A shows the breathing signature of Clement (newborn), sleeping on a BebeComfort mattress, with the sunroof closed. FIG. 9B shows the breathing signature of Viktor (newborn), sleeping on a Chicco mattress, with the sunroof closed.

At least in embodiments, the SCR-algorithm is capable of identifying the intensity and the frequency of repeating signal patterns. In case of a sleeping child, the output of this analysis will show the regularity of the breathing frequency in certain frequency range, as seen in FIGS. 9A and 9B. The algorithm will then automatically recognize the breathing signature.

Figure 10A:
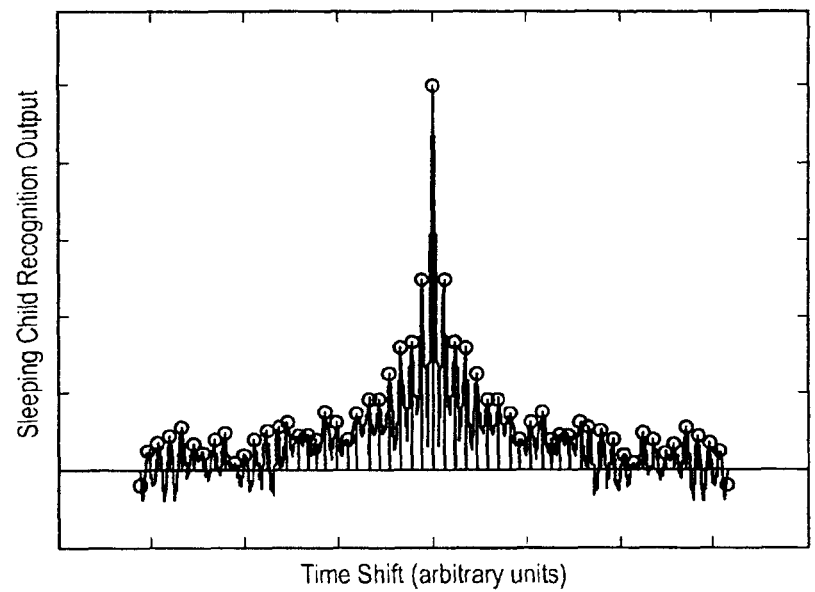
FIG. 10 includes FIGS. 10A, 10B, 10C, and 10D, which show examples of signatures for various scenarios involving external disturbances (no baby present)
Figure 10B:
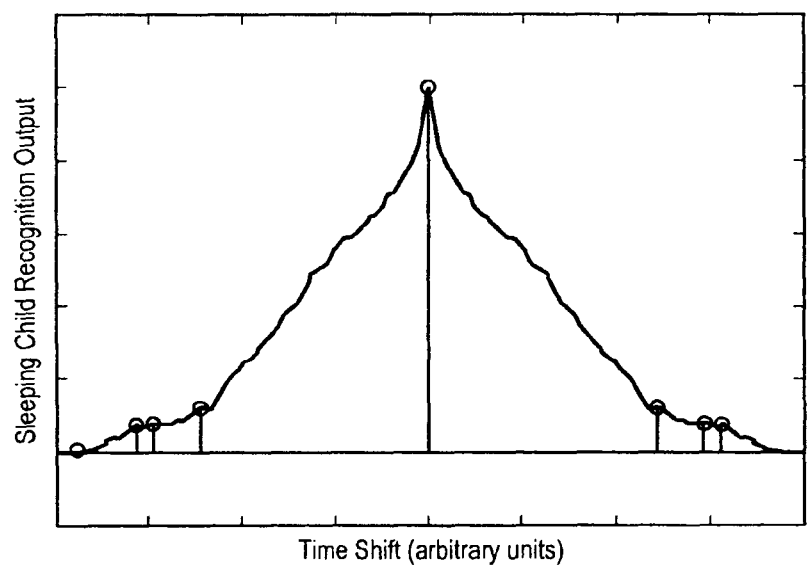
Figure 10C:
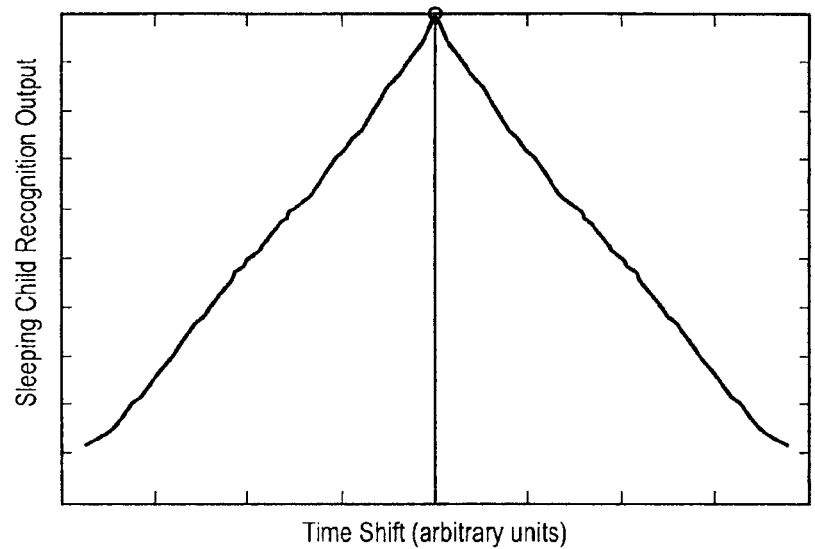
Figure 10D:
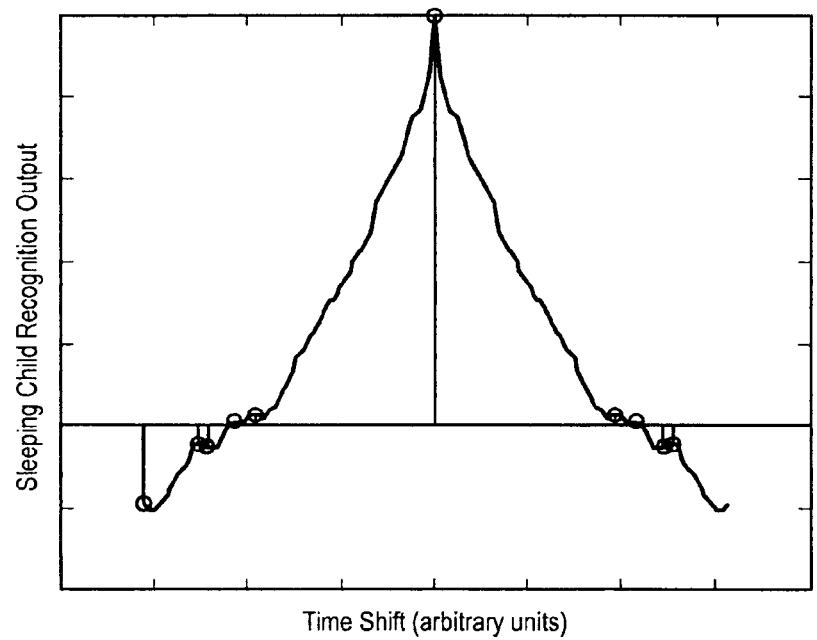

FIGS. 10A to 10D show examples of signatures for various scenarios involving external disturbances (no baby present);

In contrast to FIGS. 9A and 9B, in the case of outside influences, the output of the analysis will be very different, with extreme frequency dominance (see FIG. 10A), weak regularity (see FIG. 10B), or no periodicity at all (see FIG. 10C). FIG. 10A shows the output for a shaken Mini with a 6-Pack of water: extreme frequencies dominate which does not trigger the sleeping child decision. FIG. 10B shows the output for a BMW under a rain test: the periodicity is weak which is distinguished from the regular breathing signature. FIG. 10C shows the output for an empty seat in absence of outside influences: no periodic pattern is found in the system noise. FIG. 10D shows the output for a light metalized plastic influence: the periodicity is weak and irregular.

Returning to FIG. 7, once the signature (VSM) is obtained, an X-correlation operation is performed by correlation unit 744 followed by a peak detection operation by peak detection unit 746. This results in a decision (748) as to whether the position within the vehicle that is scanned by the radar system is occupied by a sleeping/unattended child.

Figure 11:
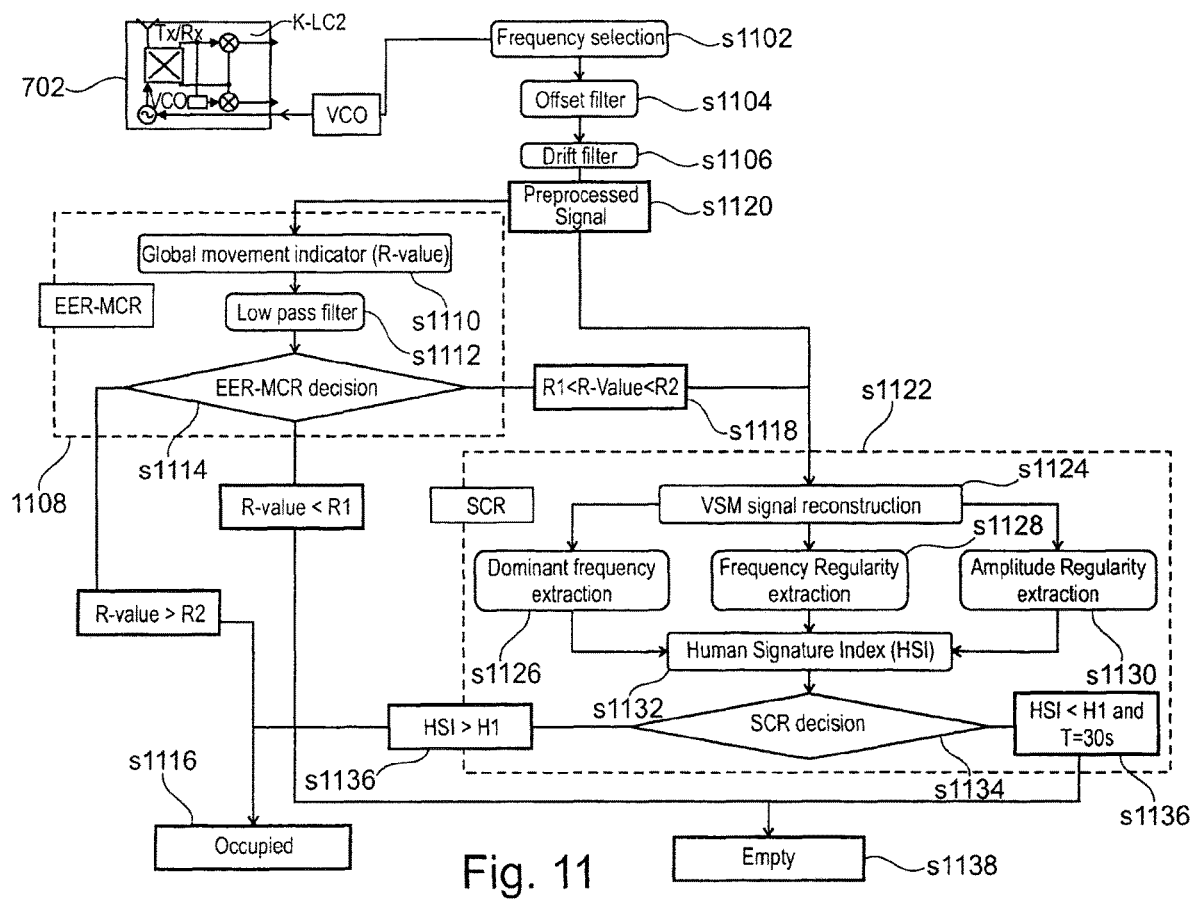
FIG. 11 is a flowchart illustrating in greater detail the algorithm processing for the purpose of sleeping child recognition in accordance with an embodiment of the invention.

FIG. 11 is a flowchart illustrating in greater detail the algorithm processing for the purpose of sleeping child recognition in accordance with an embodiment of the invention.

As will be appreciated, frequency selection s1102, offset filter ring s1104 and drift filtering s1106 correspond to units 706, 726 and 728 in FIG. 7. Further, as alluded to in relation to FIG. 7, EER-MCR subprocess 1108 involves determination of R-value s1110, low pass filtering thereof at s1112 and a EER-MCR decision at s1114; and, as indicated earlier, an R-value greater than $R_2$ gives an indication that the vehicle is occupied (s1116). In addition, a finding that the R-value is between $R_1$ and $R_2$ (s1118) means that the pre-processed signals are fed (s1120) to sleeping child recognition sub-process s1122.

For sleeping child recognition/detection, first VSM signal reconstruction is performed to generate the signature or VSM (s1124). In this embodiment, operations are carried out in parallel to perform, on the signatures, dominant frequency extraction (s1126), frequency regularity extraction (s1128) and amplitude regularity extraction (s1130). The output of operations s1126 to s1130 is a human signature index (HSI), as determined at s1132. Then, a decision is made (s1134), whereby if the HSI is greater than a threshold (H1), there is a finding (s1136) that the vehicle is unoccupied. On the other hand, if it is determined at s1134 that the HSI is less than H1 and that a period (e.g. 30 seconds; s1136) has elapsed, there is a finding that the vehicle is empty (s1138).

The Human Signature Index (HSI) determination is based on extraction of repeating patterns. This assists in determining whether a sleeping child is present, and in this respect reference is made to FIG. 12 which shows resting breathing rates for humans of various ages.

Moreover, the dominant frequency extraction operation (s1126) enables the derivation of a breathing rate index from the received signature; this is illustrated in FIG. 13A. FIG. 13B shows the distribution of the breathing variability index.

Figure 14:
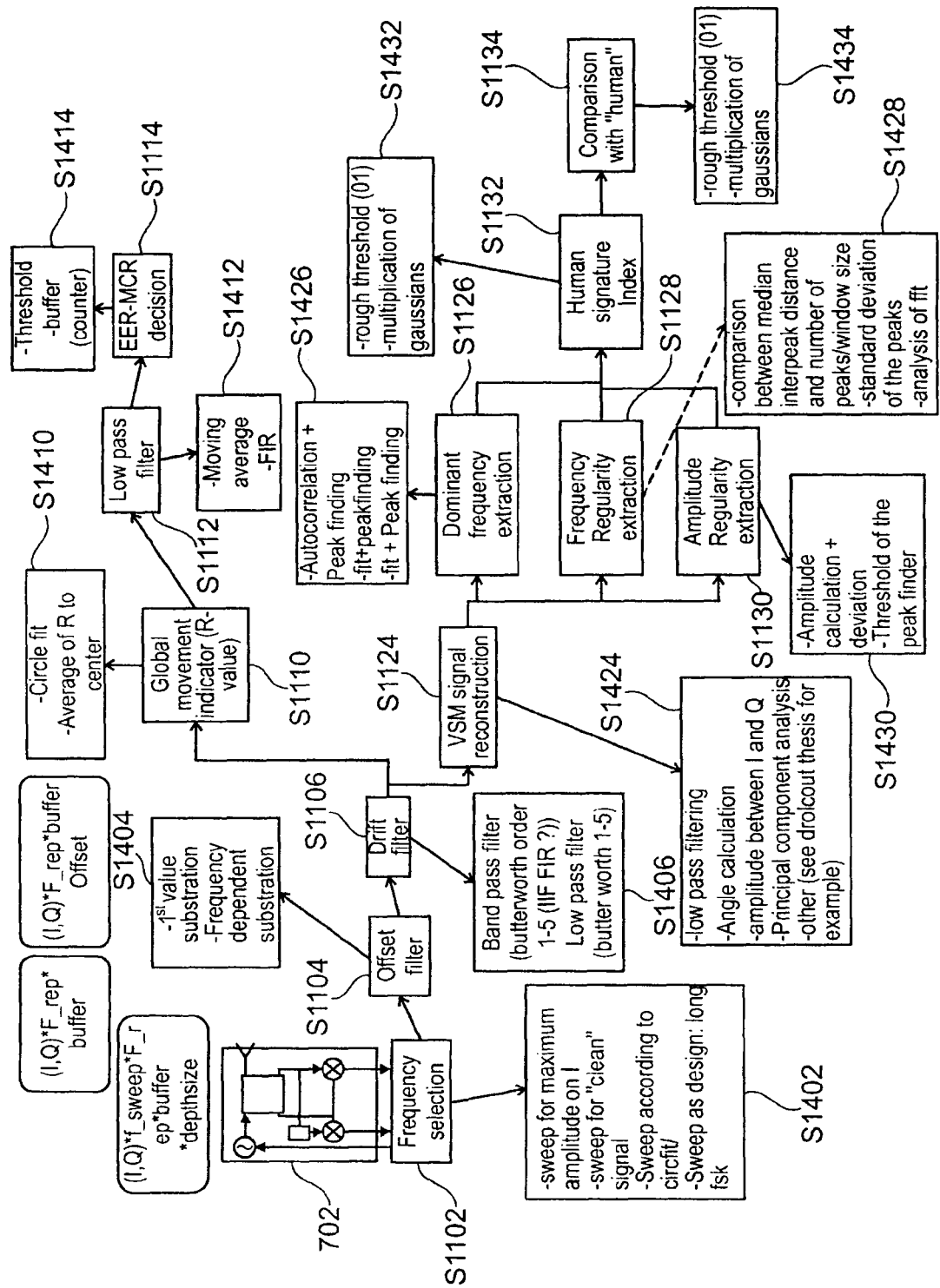
FIG. 14 shows in more detail the algorithm processing of FIG. 11.

FIG. 14 shows in more detail the algorithm processing of FIG. 11. Thus, frequency selection s1102 which acts in conjunction with analog transceiver unit 702, is operable to perform various actions in use: these may include any of or all of sweeping for maximum amplitude on I; sweeping for a "clean" signal; sweeping according to circle fitting; and sweeping for the purpose of long frequency shift keying (s1402). Further, offset filtering s1104 may involve performing one or more of first value substration and frequency dependent substration (s1404). In addition, drift filtering s1106 may comprise band pass filtering with a first to 5th order Butterworth filter and/or low pass filtering with a first to 5th order Butterworth filter (s1406). The global movement indicator (R-value determination (s1110)) may comprise circle fitting and averaging of R to the centre (s1410). The low pass filtering (s1112) may comprise such filtering based on moving average and/or FIR (s1412).

In relation to the SCR subprocess (s1122) of FIG. 11, the VSM signal reconstruction operation s1124 in FIG. 14 may comprise low pass filtering of the signature, angle calculation, determination of amplitude between I and Q, principal component analysis and/or other operations such as that according to DROITCOURT (s1424). Further, the dominant frequency extraction s1126 may comprise autocorrelation and peak finding, FFT and peak finding, or FIT and peak finding (s1426). In addition, the frequency regularity extraction operation (s1128) may comprise (s1428) comparison between median interpeak distance and the number of peaks/window size, standard deviation of the peaks, and/or analysis of FFT. Finally, the amplitude regularity extraction operation (ss1130) may comprise calculation of amplitude and deviation and/or deviation of the threshold of the peak finder (s1430). The HSI determination (s1132) may comprise (s1432) rough thresholding of the received parameters and multiplication of the Gaussians (see FIGS. 13A and 13B). Finally, the SCR decision step (s1134) (i.e. comparison with a "human") may comprise performing rough thresholding and multiplication of the Gaussians (s1434).

FIG. 15 shows signals produced using the algorithm of FIG. 14, in a case where a baby is present. The pre-processed signals output by drift filter at s1106 (FIG. 14) are indicated in FIG. 15A and the corresponding signature output by VSM signal reconstruction operation s1124 are indicated in FIG. 15B. The detected breathing rate is 53 bpm, with a good breathing pattern. The HSI is determined to be 55, i.e. greater than 20 indicating presence of a sleeping/unattended child; and confident detection within 10 seconds is obtained.

Figure shows signals produced using the algorithm of FIG. 14, in a case of a rain test with an empty car. The pre-processed signals output by drift filter at s1106 (FIG. 14) are indicated in the left-hand chart and the corresponding signature output by VSM signal reconstruction operation s1124 are indicated in the right-hand chart. In this case, no breathing is detected, the breathing rate is void, and the determined HSI is 0, i.e. less than the threshold of 20. In this case, after 30 seconds, the algorithm will stay in the "empty" state.

Timings of the SCR Algorithm:

At least in embodiments, the in practice, the Sleeping Child Recognition algorithm triggers the decision "Sleeping Child" as soon as the signature is recognized. At best, a sleeping child can then be detected within c. 30 seconds.

Moreover, to cover all possible scenarios, the Empty/Sleeping Child Threshold (EER) and the Sleeping/Moving Child Threshold (SCR) are still tested in parallel to the Sleeping Child Recognition algorithm and can also lead to anticipated decision, at least in embodiments of the invention.

This optimization of the detection time may be done for the Moving Child, Empty Seat and Sleeping Child decisions, but in case of persistent Outside Influence, the decision may only be taken after a longer period (c. 1-5 minutes).

In some embodiments, the SCR algorithm is based on two important processes: (i) the optimization of radar signals to the primary target (e.g. a baby in an occupiable position) and (ii) the recognition of human breathing signatures.

At least in embodiments, the optimization of radar signals to the primary target is the process of combining the signals of different frequency steps of the FMCW or FSK in order to eliminate the destructing interferences and retain only the best signals corresponding to the motion of the primary target. This selection process of the frequency can lead to a modification of the emitted (transmitted) radar waves if necessary.

At least in embodiments, the recognition of human breathing signals is done by using signal processing methods able to identify repetitive patterns (typically autocorrelation) on a well chosen time window (typically 15 s). From this processed output (see FIGS. 9A, 9B, 15A, 15B, 16A, and 16B), the dominant frequencies are calculated, along with their intensity and regularity. The human breathing signals are then characterized by a very regular frequency dominance of high intensity. For instance, the frequency of human breathing is typically between 15 (adults) and 70 (newborns) breaths per minute. The regularity is found out by determining if the frequency is still valid on a longer time range (and not simply the first harmonics). The intensity of the frequency dominance should also not deviate more than a typical amount during the time window of analysis.

While embodiments have been described by reference to embodiments having various components in their respective implementations, it will be appreciated that other embodiments make use of other combinations and permutations of these and other components.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Thus, while there has been described what are believed to be the preferred embodiments of the invention, those skilled in the art will recognize that other and further modifications may be made thereto without departing from the spirit and scope of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A radar sensor system for a vehicle, the system comprising:
   a transmitter, for illuminating at least one occupiable position within the vehicle with radiation, the radiation exhibiting multiple frequencies;
   at least one sensor for generating radar sensor signals from radiation reflected as a result of the transmitted radiation, a plurality of the radar sensor signals corresponding to different frequencies;
   processing circuitry, coupled to the at least one sensor, the processing circuitry being configured to carry out the steps of:
      generating, based on the radar sensor signals, a first indicator value, the first indicator value indicating a degree of motion associated with the occupiable position;
      determining whether the first indicator value satisfies a first predetermined criteria; and
      when the first indicator value satisfies the first predetermined criteria, generating, based on radar sensor signals, a second indicator value indicating a degree of repetitive pattern within the radar sensor signals, wherein the second indicator value is, or is derived from, the product of multiple breathing indices, each breathing index being related to breathing rate.

2. The radar sensor system of claim 1, wherein the first predetermined criteria is that the first indicator value lies between a first threshold value and a second threshold value.

3. The radar sensor system of claim 2, wherein
   (i) the first threshold value is such that the first indicator value being below the first threshold value is indicative of an empty seat or environment;
   (ii) the second threshold value is such that the first indicator value being above the second threshold value is indicative of a moving person or child; and
   (iii) the first threshold value and the second threshold value are such that the first indicator value being between the first threshold value and the second threshold value is indicative of a sleeping child being present in the occupiable position or of an influence from sources external to the vehicle.

4. The radar sensor system of claim 1, wherein the first indicator value is based on an amplitude of the radar sensor signals.

5. The radar sensor system of claim 1, including the step of determining that a child is present with respect to the at least one occupiable position within the vehicle when the second indicator value satisfies a second predetermined criteria.

6. The radar sensor system of claim 5, wherein the first predetermined criteria is that the first indicator value lies between a first threshold value and a second threshold value, and wherein the second predetermined criteria is that the second indicator value lies above a third threshold value.

7. The radar sensor system of claim 5, wherein the frequencies of the transmitted radiation are dynamically varied such that the steps of (i) determining whether the first indicator value satisfies a first predetermined criteria and (ii) determining that a child is present with respect to the at least one occupiable position within the vehicle when the second indicator value satisfies a second predetermined criteria are periodically carried out in parallel.

8. The radar sensor system of claim 1, wherein at least one breathing rate index is derived from motion determined based on the radar sensor signals.

9. The radar sensor system of claim 1, wherein the second indicator value is dependent upon a breathing rate variation index, the breathing rate variation index being derived from motion determined based on the radar sensor signals and indicating a degree of variation in breathing rate.

10. The radar sensor system of claim 9, wherein the second indicator value is based on a combination of both the breathing rate and breathing rate variation index.

11. The radar sensor system of claim 1, wherein the second indicator value comprises a breathing signature.

12. A radar sensor system for a vehicle, the system comprising:
   a transmitter, for illuminating at least one occupiable position within the vehicle with radiation, the radiation exhibiting multiple frequencies;
   at least one sensor for generating radar sensor signals from radiation reflected as a result of the transmitted radiation, a plurality of the radar sensor signals corresponding to one or more frequencies;
   processing circuitry, coupled to the at least one sensor, the processing circuitry being configured to carry out the steps of:
      generating, based on the radar sensor signals, a first indicator value, the first indicator value indicating a degree of motion associated with the occupiable position;
      determining whether the first indicator value satisfies a first threshold;
      when the first indicator value does not satisfy the first threshold, determining that a child is not present in the vehicle;
      when the first indicator value satisfies the first threshold, determining whether the first indicator value satisfies a second threshold; and
      when the first indicator value satisfies the second threshold, determining that a child is present in the vehicle.

13. The radar sensor system of claim 12, wherein the steps of determining whether the first indicator value satisfies the first threshold and determining whether the first indicator value satisfies the second threshold are performed based on radar sensor signals occurring during a first predetermined period.

14. The radar sensor system of claim 13, wherein the first predetermined period is 5-15 seconds.

15. The radar sensor system of claim 12, wherein, when the first indicator value does not satisfy the second threshold, then generating, based on radar sensor signals, a second indicator value indicating a degree of repetitive pattern within the radar sensor signals, wherein the second indicator value is, or is derived from, the product of multiple breathing indices, each breathing index being related to breathing rate.

16. The radar sensor system of claim 15, including the step of determining that a child is present with respect to the at least one occupiable position within the vehicle when the second indicator value satisfies a second predetermined criteria.

17. The radar sensor system of claim 16, wherein the second predetermined criteria is that the second indicator value lies above a third threshold value.

18. The radar sensor system of claim 16, wherein the one or more frequencies of the transmitted radiation are dynamically varied such that the steps of (i) determining whether the first indicator value satisfies the first threshold, (ii) determining whether the first indicator value satisfies the second threshold, and (iii) determining that a child is present with respect to the at least one occupiable position within the vehicle when the second indicator value satisfies a second predetermined criteria are periodically carried out in parallel.

19. The radar sensor system of claim 12, wherein
(i) the first threshold is such that the first indicator value being below the first threshold is indicative of an empty seat or environment;
(ii) the second threshold is such that the first indicator value being above the second threshold is indicative of a moving person or child; and
(iii) the first threshold and the second threshold are such that the first indicator value being between the first threshold and the second threshold is indicative of a sleeping child being present in the occupiable position or of an influence from sources external to the vehicle.

20. A method of using a radar sensor system, the radar sensor system comprising a transmitter, at least one sensor, and processing circuitry, the method comprising:
   illuminating, using the transmitter, at least one occupiable position within a vehicle with radiation, the radiation exhibiting at least one frequency;
   generating, using at least one sensor, radar sensor signals from radiation reflected as a result of the transmitted radiation; and
   carrying out, using the processing circuitry, the following steps:
      generating, based on the radar sensor signals, a first indicator value, the first indicator value indicating a degree of motion associated with the occupiable position;
      determining whether the first indicator value satisfies a first predetermined criteria; and
      when the first indicator value satisfies the first predetermined criteria, generating, based on radar sensor signals, a second indicator value indicating a degree of repetitive pattern within the radar sensor signals, wherein the second indicator value is, or is derived from, the product of multiple breathing indices, each breathing index being related to breathing rate.

* * * * *